US00PP08379P

United States Patent [19]

Warriner, deceased et al.

[11] Patent Number: Plant 8,379

[45] Date of Patent: Sep. 21, 1993

[54] ROSE PLANT JACEX

[75] Inventors: William A. Warriner, deceased, late of Tustin, Calif., by Alene B. Warriner, executor; Keith W. Zary, Thousand Oaks, Calif.

[73] Assignee: Bear Creek Gardens, Inc., Medford, Oreg.

[21] Appl. No.: 796,452

[22] Filed: Nov. 21, 1991

[51] Int. Cl.[5] ..... A01H 5/00

[52] U.S. Cl. ..... Plt./18

[58] Field of Search ..... Plt. 18, 26, 9

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

Hybrid tea rose having light, pastel pink flowers which are long lasting on plant and as cut flower. Foliage is a glossy, dark green and resistant to powdery mildew and rust.

1 Drawing Sheet

1

The present invention relates to a new and distinct variety of rose plant of the hybird tea class which was originated by us by crossing the variety Silver Jubilee, with an unnamed seedling.

The primary objective of this breeding was to produce a new rose variety having the dark green glossy healthy foliage of Silver Jubilee combined with the large flower and heavy petal substance of the unnamed seedling. Both parents were pink so seedlings were expected to have pink blooms. The objective was substantially achieved along with other desirable improvements as videnced by the following unique combination of characteristics which are outstanding in the new variety and which distinguish it from its parents, as well as from all other varieties of which I am aware:

1. Dark green glossy disease resistant foliage;
2. Vigorous upright habit of growth;
3. Thick leathery petals;
4. None fading light, pastel pink flower color;
5. Moderate fragrance;
6. Long lasting flower both on the plant and as a cut flower.

Asexual reproduction of this new variety by budding, as performed at Wasco and Somis, Calif. shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, exept where ordinary dictionary significance of color is indicated.

Parentage:

*Seed parent.*—Silver Jubilee.

*Pollen parent.*—Unnamed.

Classification:

*Botanical.*—Rose hybrid.

*Commercial.*—Hybrid tea.

2

FLOWER

Observations made from specimens grown in a garden in Somis, Calif., Apr.-Jun. 1991.

Blooming habit: Recurrent.

Bud:

*Size.*—1½" when the petals start to unfurl.

*Form.*—Pointed ovoid.

*Color.*—When sepals first divide, bud color is Red Group 49A. When half blown, the upper sides of the petals are Red Group 49C; and the lower sides of the petals are Red Group 49C.

*Sepals.*—Color: Green Group 138C but with some reddish cast. Surface texture: Covered in fine hair. There are three heavily appendaged sepals. There are two unappendaged sepals with hairy edges.

*Receptacle.*—Color: Green Group 143C. Shape: Funnel. Size: Small (⅜"×⅜"). Surface: Smooth.

*Peduncle.*—Length: 2½". Surface: Glandular. Color: Medium green. Strength: Stiff, erect.

Bloom:

*Size.*—Large. Average open size is 5 inches.

*Borne.*—Singly.

*Stems.*—Medium, strong, 14–16".

*Form.*—When first open: High centered. Permanence: Retains its form to the end, outer petals curl back.

*Petalage.*—Number of petals under normal conditions: 35–40.

*Color.*—The upper side of the petals is Red Group 49C. The reverse side of the petals is Red Group 49C. At the base of petals is fairly large yellow hair half moon, about ½"×½", of Yellow Group 13A. The major color on the upper side is Red Group 49C.

*Variegations.*—None.

*Discoloration.*—At the end of the third day, none.

*Fragrance.*—Moderate.

Petals:

*Texture.*—Thick, leathery.

*Shape.*—Deltoid.

*Form.*—Tips slightly recurved.

*Arrangement.*—Imbricated, with a few petaloids in the center.

*Persistence.*—Drop off cleanly.

*Lastingness.*—On the plant: Long, 5–6 days. As a cut flower: Long, 6–8 days.

Reproductive Parts:

*Anthers.*—Size: Large. Quantity: Many. Color: Yellow. Arrangement: Regular around styles.

*Filaments.*—Color: Yellow.

*Pollen.*—Color: Lemon-yellow.

*Styles.*—Color: Reddish.

*Stigmas.*—Color: Greenish-white.

Form: Bush.

Growth: Vigorous, upright, branching.

Foliage:

*Number of leaflets on normal mid-stem leaves.*—5.

*Size.*—Large, 6″×5″.

*Quantity.*—Abundant.

*Color.*—New foliage: Dark red. Old foliage: Glassy, dark green.

Leaflets:

*Shape.*—Broadly oval.

*Texture.*—Upper side: Leathery, glossy.

*Edge.*—Serrated.

*Serration.*—Single.

*Petiole rachis.*—Color: Reddish.

*Petiole underside.*—Rough, with prickles.

*Stipules.*—Medium, ½″, bearded.

*Disease resistance.*—Resistant to rust and mildew under normal growing conditions at Somis, Calif.

Wood:

*New wood.*—Color: Reddish-green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. on laterals: None.

It is claimed:

1. A new and distinct variety of rose plant of the hybrid tea class, substantially as herein shown and described, characterized particularly as to novelty by the unique combination of its high level of disease resistance, its long lasting blooms, its non-fading pastel pink flower color, its vigorous upright growth, its moderate fragrance and its leathery, thick petals.

* * * * *

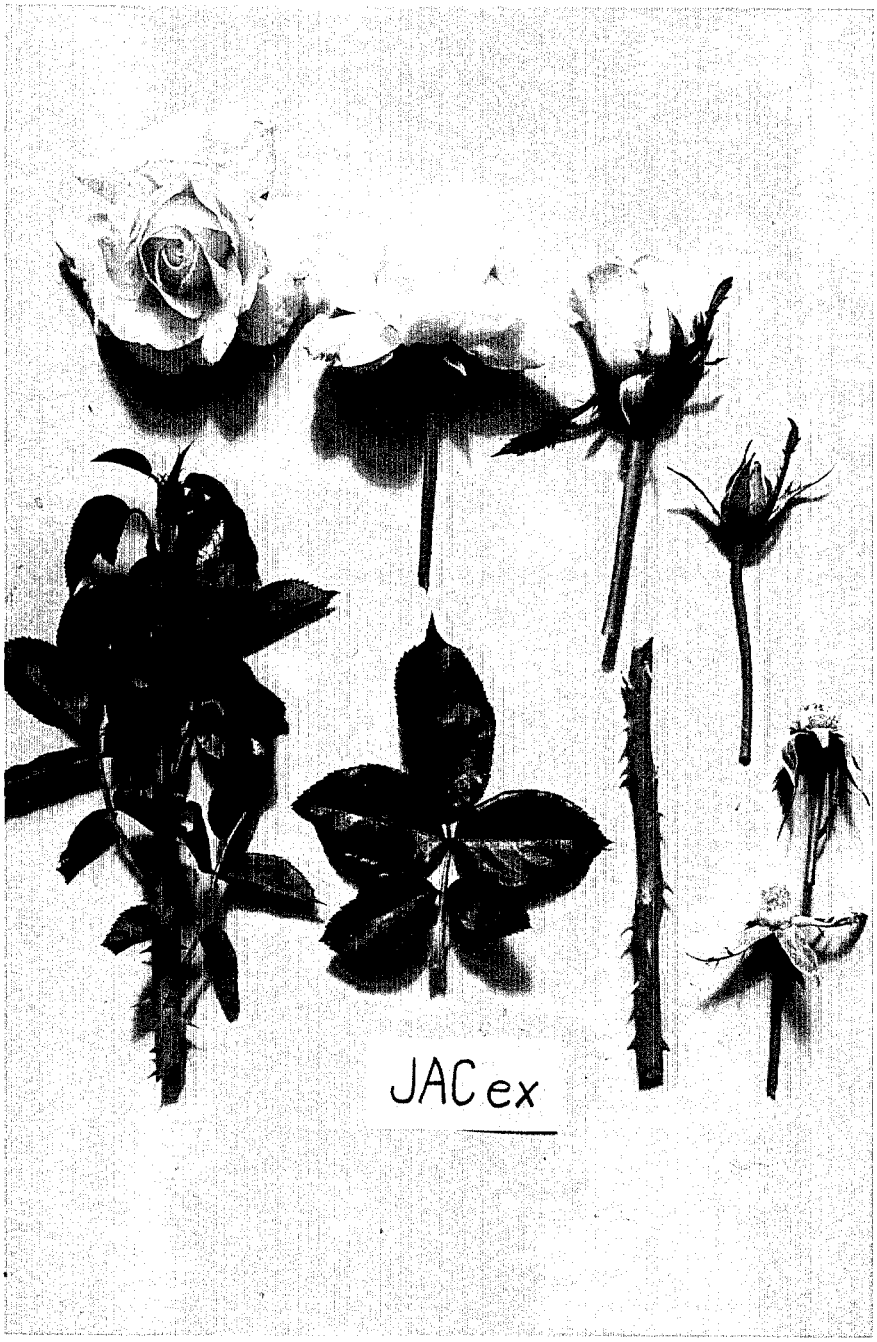
JAC ex